United States Patent
Takashima (10) Patent No.: US 7,015,818 B2
(45) Date of Patent: Mar. 21, 2006

(54) DOZE ALARM FOR DRIVER USING ENCLOSED AIR SOUND SENSOR

(75) Inventor: Mitsuru Takashima, Tokyo (JP)

(73) Assignee: M.I. Laboratories Corporation, Tokyo (JP)

(*) Notice: Subject to any disclaimer, the term of this patent is extended or adjusted under 35 U.S.C. 154(b) by 361 days.

(21) Appl. No.: 10/362,495

(22) PCT Filed: Jan. 22, 2002

(86) PCT No.: PCT/JP02/00436

§ 371 (c)(1),
(2), (4) Date: Feb. 21, 2003

(87) PCT Pub. No.: WO03/061476

PCT Pub. Date: Jul. 31, 2003

(65) Prior Publication Data

US 2004/0061615 A1  Apr. 1, 2004

(51) Int. Cl.
*G08B 23/00* (2006.01)

(52) U.S. Cl. .................. 340/576; 340/429; 340/439

(58) Field of Classification Search ............. 340/576, 340/429, 439
See application file for complete search history.

(56) References Cited

U.S. PATENT DOCUMENTS

| | | | | |
|---|---|---|---|---|
| 4,031,527 A | * | 6/1977 | Yanagishima et al. | 340/576 |
| 5,127,708 A | | 7/1992 | Kishi et al. | |
| 5,404,128 A | * | 4/1995 | Ogino et al. | 340/425.5 |
| 5,574,641 A | * | 11/1996 | Kawakami et al. | 701/1 |
| 5,585,785 A | * | 12/1996 | Gwin et al. | 340/575 |
| 6,506,153 B1 | * | 1/2003 | Littek et al. | 600/301 |
| 6,575,902 B1 | * | 6/2003 | Burton | 600/300 |
| 6,756,903 B1 | * | 6/2004 | Omry et al. | 340/576 |

* cited by examiner

Primary Examiner—Thomas J. Mullen, Jr.
Assistant Examiner—Son Tang
(74) Attorney, Agent, or Firm—Robert D. Katz, Esq.; Cooper & Dunham LLP (57) ABSTRACT

A closed pneumatic sound sensor is incorporated in a driver's seat and catches a signal representative of a movement of the body of the driver, and a continuation time period within which the level of the signal does not reach a fixed level is detected.

Simultaneously, a signal which is generated only when the vehicle is running is caught from the vehicle, and the two signals are compared with each other by an arithmetic operation circuit. Only when both of the signals are present and a particular tendency appears in the continuation time period of the signal representative of a movement of the body, an alarm is generated.

A less expensive doze-at-the-wheel alarming apparatus which does not require cumbersome mounting and does not operate when the vehicle is not running is provided.

15 Claims, 13 Drawing Sheets

DOZE ALARM FOR DRIVER USING ENCLOSED AIR SOUND SENSOR

TECHNICAL FIELD

This invention relates to a doze alarming apparatus for a driver of a vehicle which is driven by a driver such as an automobile, a train, a ship or an aircraft, and more particularly to an apparatus which detects a "driver's consciousness decline" state immediately before the driver falls into a doze from a variation of the physical movement involved in a driving operation of the driver and makes the driver awakening.

BACKGROUND ART

As a conventional doze-at-the-wheel alarming apparatus, methods of detecting meandering of a car, supervising the variation of the driver's eye point from an image process of camera images, detecting a variation of biological information such as the heart beat, breath or the like of the driver using electrodes, sensors or the like attached to the driver, and so forth have been proposed.

Such apparatus as described above have problems that they are expensive, that it is cumbersome for the driver to attach them, that they restrict the behavior of the driver, that they operate also when the vehicle is not running and so forth.

DISCLOSURE OF THE INVENTION

The present invention contemplates, with note taken of the fact that the general physical movement of a human being including movements of the hands, feet, neck and body involved in a driving operation has a characteristic difference between that when the human being is awakening and that in a state (driving consciousness decline state) immediately before a doze state is entered, prevention of a doze-at-the-wheel accident by detecting the difference and issuing an alarm to the driver.

The inventor of the present invention has developed various biological information collection apparatus which use a closed pneumatic sound sensor which detects the pneumatic pressure in an closed air chamber made of airtight flexible rubber, plastics, metal, cloth, paper or the like by means of a non-directional microphone or a pressure sensor and converts the pneumatic pressure into an electric signal.

Since a closed pneumatic sound sensor of the type described can be incorporated readily in a bed, a chair, a bath tab, a toilet seat and so forth, it has been proposed already to use the closed pneumatic sound sensor for such locations to collect biological information of the heart beat, breath and so forth of an animal including a human being to grasp the state of health.

Also a method has been proposed wherein a closed pneumatic sound sensor of the type described is incorporated in a bed and detects a signal having a long interval and a great amplitude like a signal of tossing and turning to supervise a sleep state of a human being.

According to the present invention, a physical movement, which has a comparatively long period and does not have a great amplitude and which does not apply to any of the above cases, is observed continuously and successively in delimited units of a fixed period of time using a closed pneumatic sound sensor, and when characteristic continuation of a signal indicative of a driving consciousness decline state occurs, then an alarm is issued immediately.

BEST MODE FOR CARRYING OUT THE INVENTION

Since the present invention relates to an apparatus which is rendered operative during driving, particularly while a vehicle is running, it is necessary to detect, in addition to signals involved in a physical movement of the human body, a signal representative of driving of the vehicle and so forth and permit operation of an alarm only when the signal is present.

As a method of obtaining a signal representing that a vehicle or the like is in operation:

1. a method of separating the signal from a signal, within which a physical movement signal is mixed, obtained by the closed pneumatic sound sensor; and 2. a method of directly detecting the signal from a variation in voltage or current in an electric circuit of the vehicle; are available.

Further, as a reading method of a signal involved in a physical movement:

A. a method of measuring, with note taken of a wave height of an output signal of the closed pneumatic sound sensor, the signal depending upon the presence or absence of a signal having a level higher than a fixed level per unit period of time; and B. a method of determining a standard deviation of an output of an output signal of the closed pneumatic sound sensor per unit period of time and discriminating the signal based on the value of the standard deviation; are available.

Furthermore, as a type of an alarm to be provided to the driver:

a. a vibrator is used to impart vibrations directly to the body;

b. a buzzer is used to emit an alarm sound;

c. a speaker is used to emit a voice alarm;

d. blinking of light;

e. sudden cooling operation of an air conditioner; and so forth are available. The present invention can be implemented by suitably combining the means of the items 1, 2, A, B, a, b, c, d, e and so forth given above.

Figure 1:
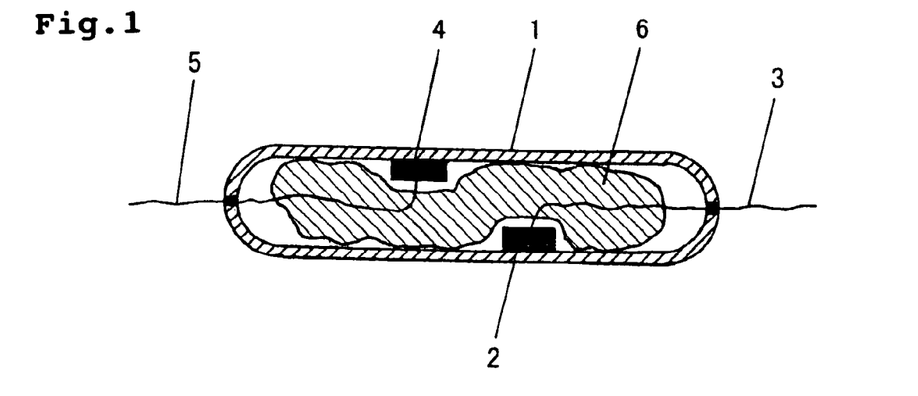
FIG. 1 is a sectional view showing the structure of a closed pneumatic sound sensor.

FIG. 1 is a sectional view showing the structure of a closed pneumatic sound sensor used in an apparatus of the present invention.

Reference numeral 1 denotes a closed airbag or cabinet made of rubber, plastics, metal, cloth, paper or the like, and a non-directional microphone or pressure sensor 2 is attached in the inside of the closed airbag or cabinet 1 such that an electric signal of the non-directional microphone or pressure sensor 2 can be extracted to the outside by a cord 3.

Reference numeral 4 denotes an alarm unit such as a vibrator or a speaker, and an alarm signal is sent from the outside to the alarm unit 4 through a cord 5. The alarm unit 4 need not necessarily be placed in the inside of the closed airbag or cabinet, but may be placed outside only if an alarm is imparted from the alarm unit 4 to the driver.

Since such a weight as the body weight is applied to the closed airbag or cabinet 1, in order to protect internal elements, a resilient reinforcing material 6 such as sponge should be used to reinforce the inside of the closed airbag or cabinet 1 as occasion demands.

Figure 2:
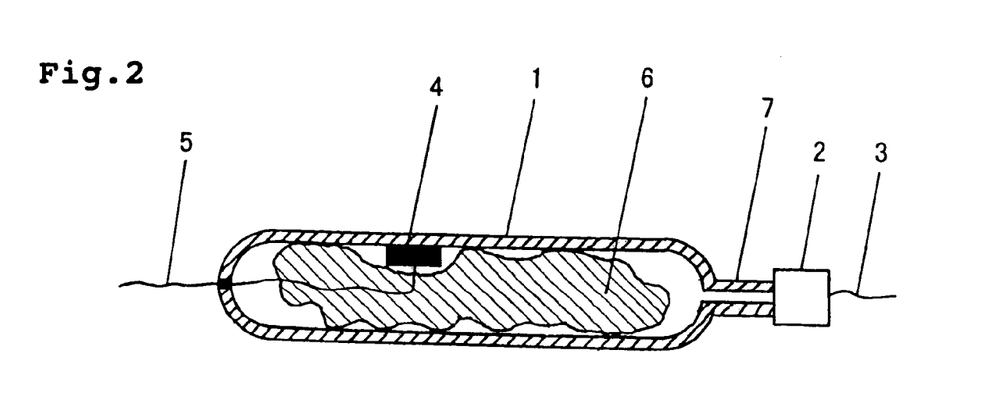
FIG. 2 is a sectional view showing the structure of another closed pneumatic sound sensor.

FIG. 2 is a sectional view showing the structure of another embodiment of the closed pneumatic sound sensor used in the apparatus of the present invention, and like elements are denoted by like reference numerals in FIG. 1.

In the present embodiment, the non-directional microphone or pressure sensor 2 is placed outside the closed airbag or cabinet 1, and air in the closed airbag or cabinet 1 is introduced to the non-directional microphone or pressure sensor 2 through a pipe 7.

Figure 3:
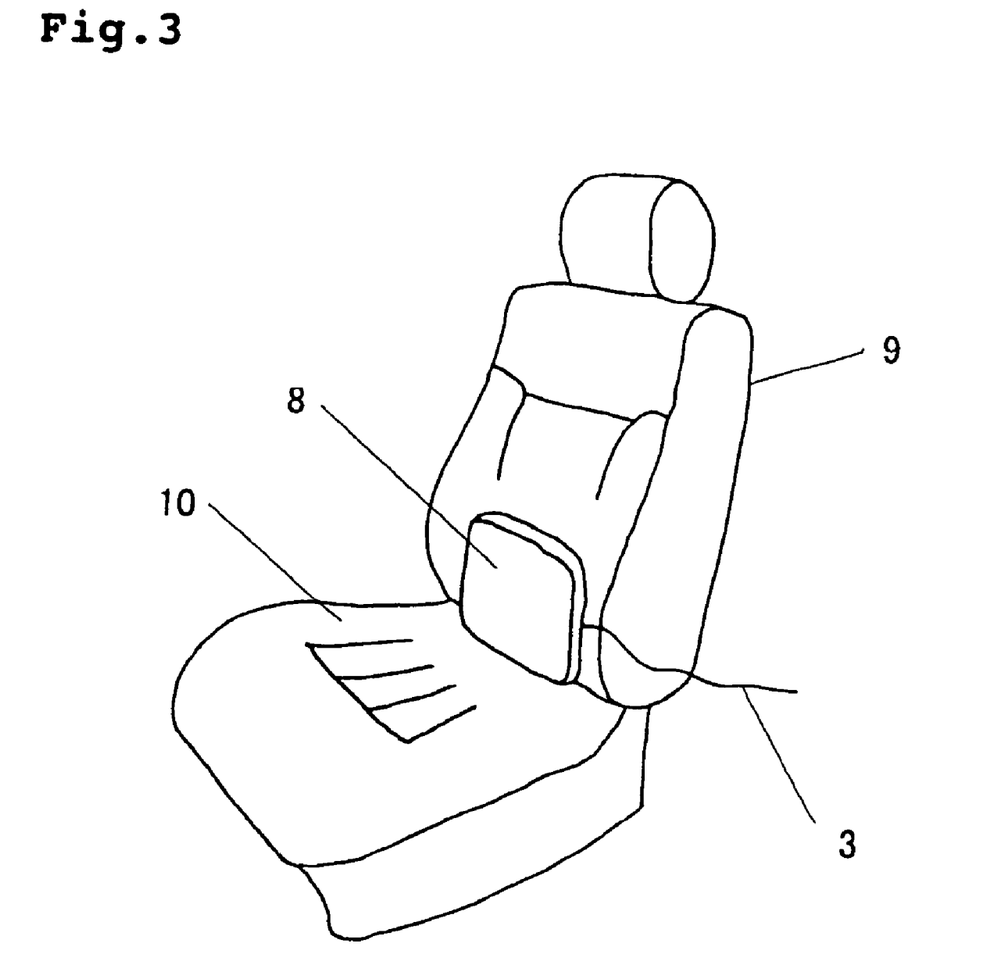
FIG. 3 is a view wherein the closed pneumatic sound sensor is attached to a driver's seat.

FIG. 3 shows an example wherein the closed pneumatic sound sensor described with reference to FIG. 1 or 2 is attached to a driver's seat of an automobile.

In the example of FIG. 3, the closed pneumatic sound sensor 8 is attached to a backrest 9 so that it may be used also as a cushion. However, the closed pneumatic sound sensor 8 can be embedded on an internal surface of the backrest 9. Similarly, the closed pneumatic sound sensor 8 may be placed on a seat 10, or also it is possible to embed the closed pneumatic sound sensor 8 in the inside of the seat 10.

Further, a plurality of closed pneumatic sound sensors may be arranged in a juxtaposed relationship to each other or may be used for both of the backrest 9 and the seat 10.

Reference numeral 3 denotes a cord for extracting an output of the closed pneumatic sound sensor to the outside.

Figure 4:
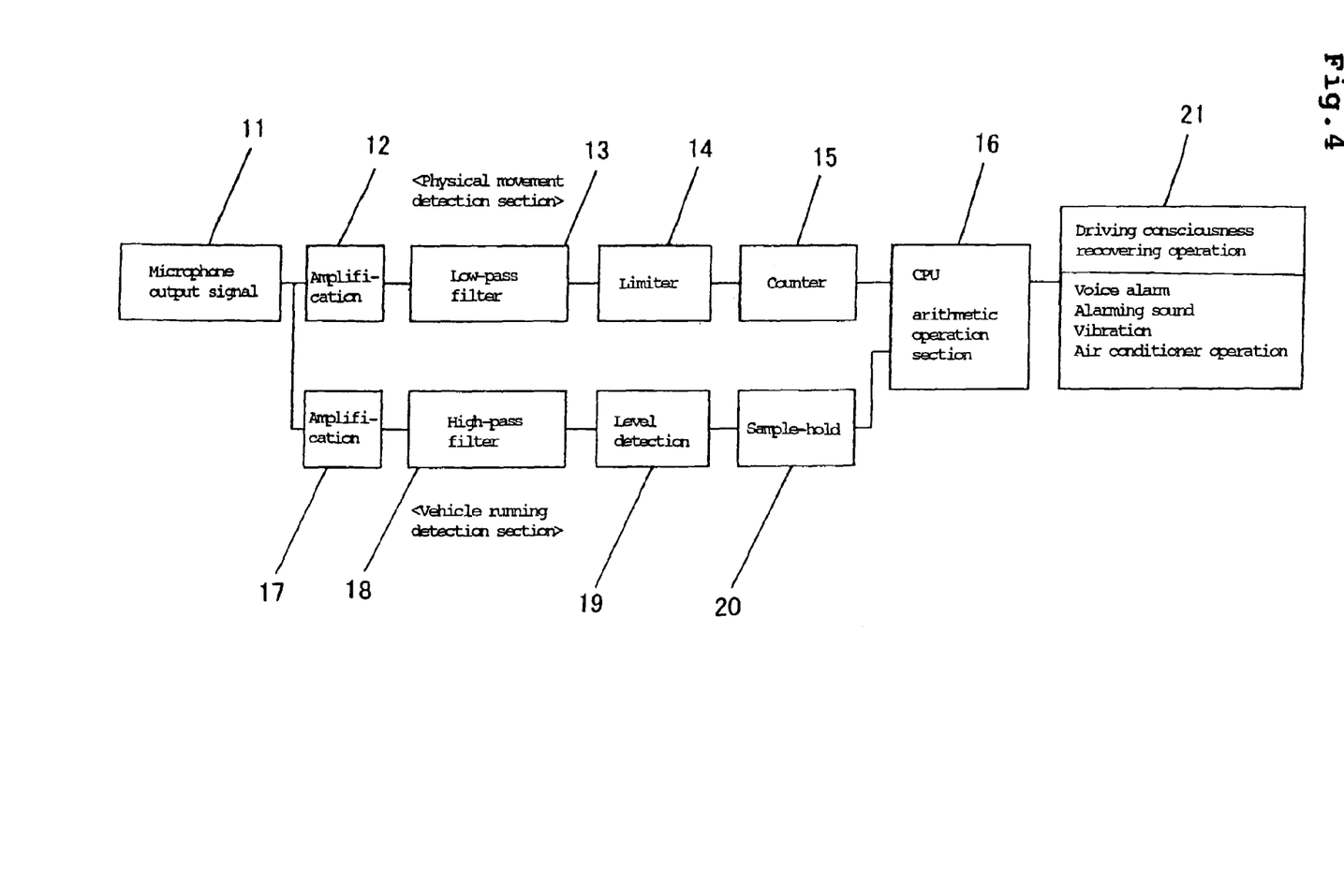
FIG. 4 is a circuit diagram of a circuit for processing an output of the closed pneumatic sound sensor.

FIG. 4 is a block diagram showing an example of a circuit which detects a signal upon driving consciousness decline from an output of the closed pneumatic sound sensor and changing the signal into an alarm signal.

Reference numeral 11 denotes an output signal of the closed pneumatic sound sensor, and after the output signal 11 is amplified by an amplifier 12, only low frequency components representative of a physical movement in the output signal are filtered by a low-pass filter 13.

Reference numeral 14 denotes a limiter, and this is operated, for example, with ±200 mV to count the number of signals which exceed ±200 mV by means of a counter 15.

A signal of the counter number is applied to an arithmetic operation section 16.

Meanwhile, part of the output signal 11 of the closed pneumatic sound sensor is amplified by an amplifier 17, and then high frequency components which are produced upon running of the vehicle are filtered by a high-pass filter 18.

The filtered signal is applied to a level detector 19 and then converted into a digital signal by a sample-hold circuit 20, whereafter it is applied to the arithmetic operation section 16.

The arithmetic operation section 16 discriminates a case wherein the number of outputs of the counter 15 per unit period of time exhibits a fixed tendency and a signal produced by driving of the vehicle is present, and generates a signal for operating an alarm unit 21.

Figure 5:
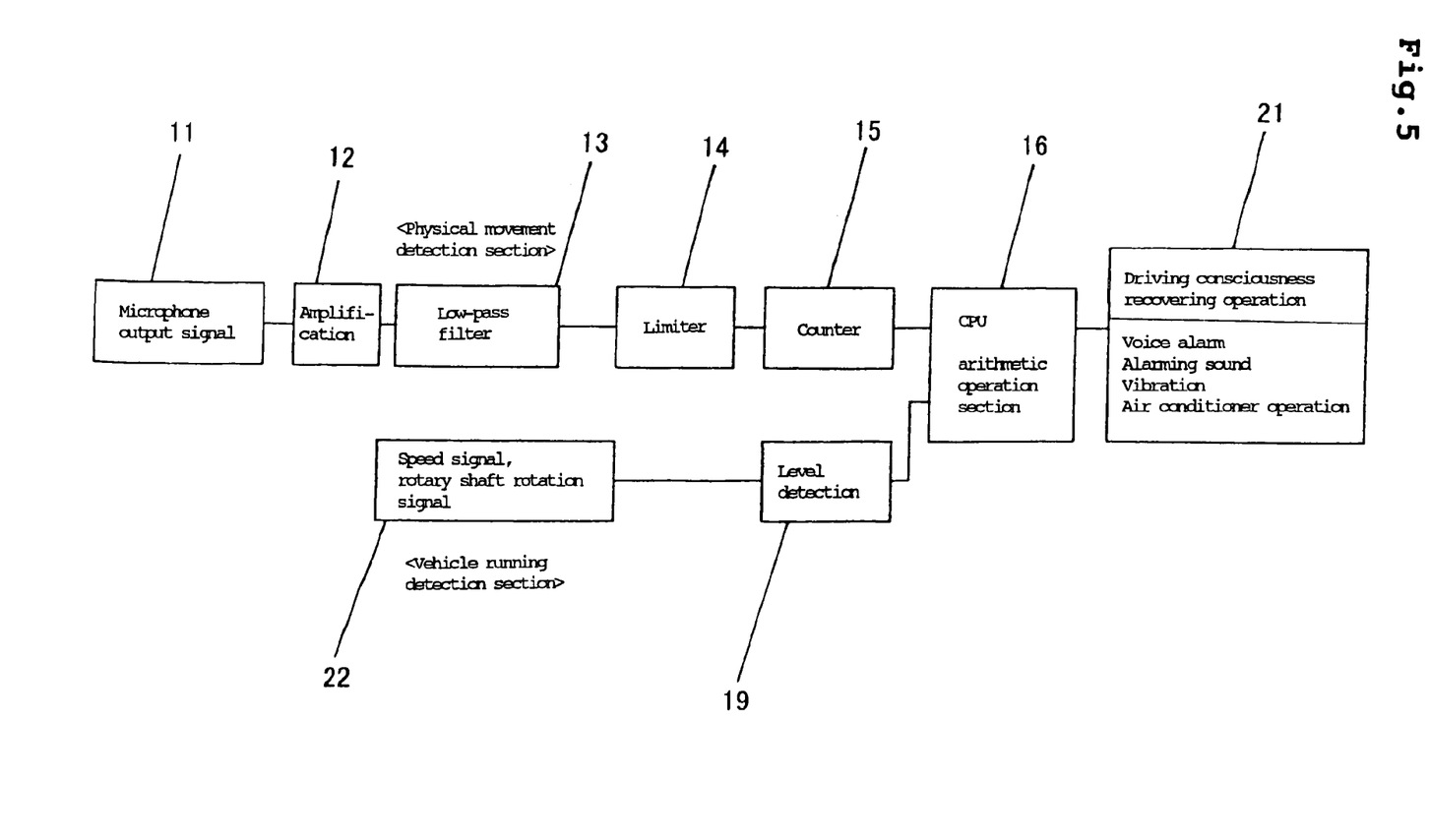
FIG. 5 is a circuit diagram of another circuit for processing an output of the closed pneumatic sound sensor.

FIG. 5 is a block diagram of a circuit where a signal representing that the vehicle is running is extracted from an electric circuit of the vehicle, and like elements to those of FIG. 4 are denoted by like reference numerals.

In the present example, a signal 22 representing that the vehicle is operating is introduced, for example, from an electric circuit of a speedometer directly to the level detector 19 and then applied to the arithmetic operation section 16. The other operation is similar to that in FIG. 4.

Figure 6:
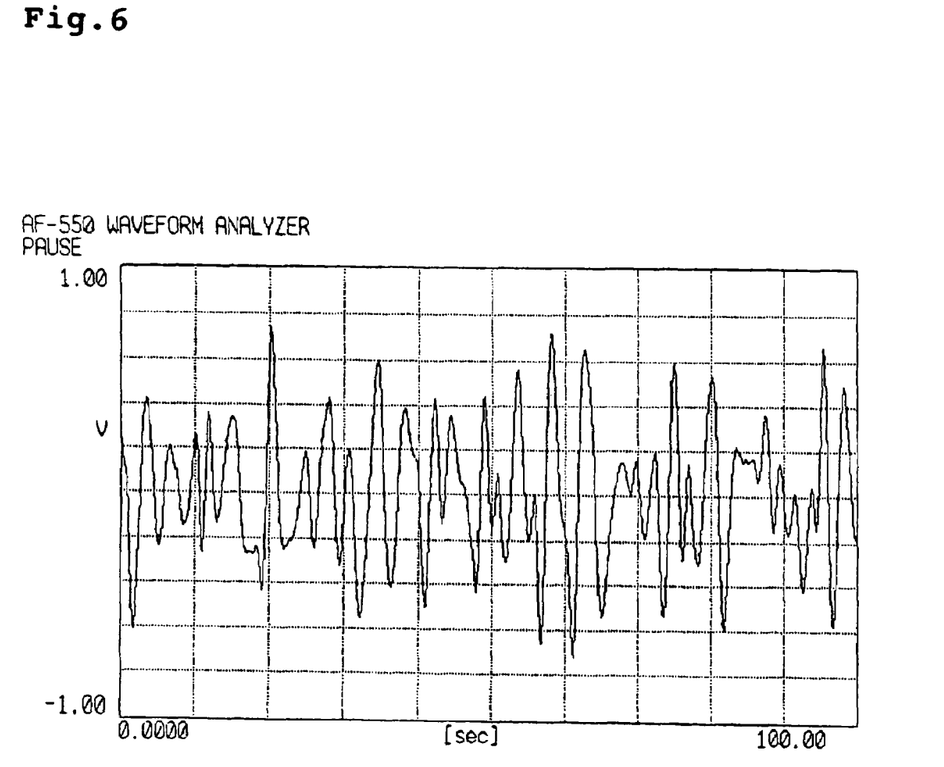
FIG. 6 is a graph illustrating an output of a signal representative of a physical movement in an awakening state.
Figure 7:
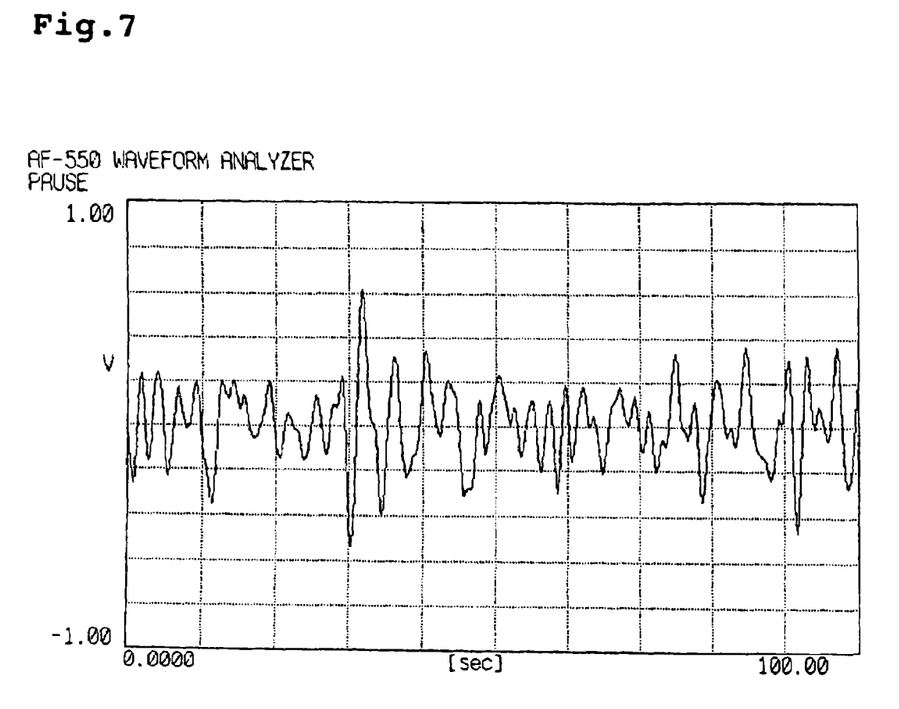
FIG. 7 is a graph illustrating an output of a signal representative of a physical movement in a driving consciousness decline state.

FIGS. 6 and 7 are graphs illustrating an example of outputs of the low-pass filters 13 of the circuits of FIGS. 4 and 5, and FIG. 6 shows the output when the driver is awakening while FIG. 7 shows the output in a driving consciousness decline state.

In the graphs, the axis of ordinate indicates the output in millivolt (mV), and the axis of abscissa indicates the time in second.

As can be seen apparently from the figures, the output of the signal representative of the physical movement of the driver exhibits a great difference between that in an awakening state and that in a driving consciousness decline state, and if the number of waves of the signal which exceed, for example, ±200 mV within a unit period of time, then the driving consciousness decline state can be detected readily.

Figure 8:
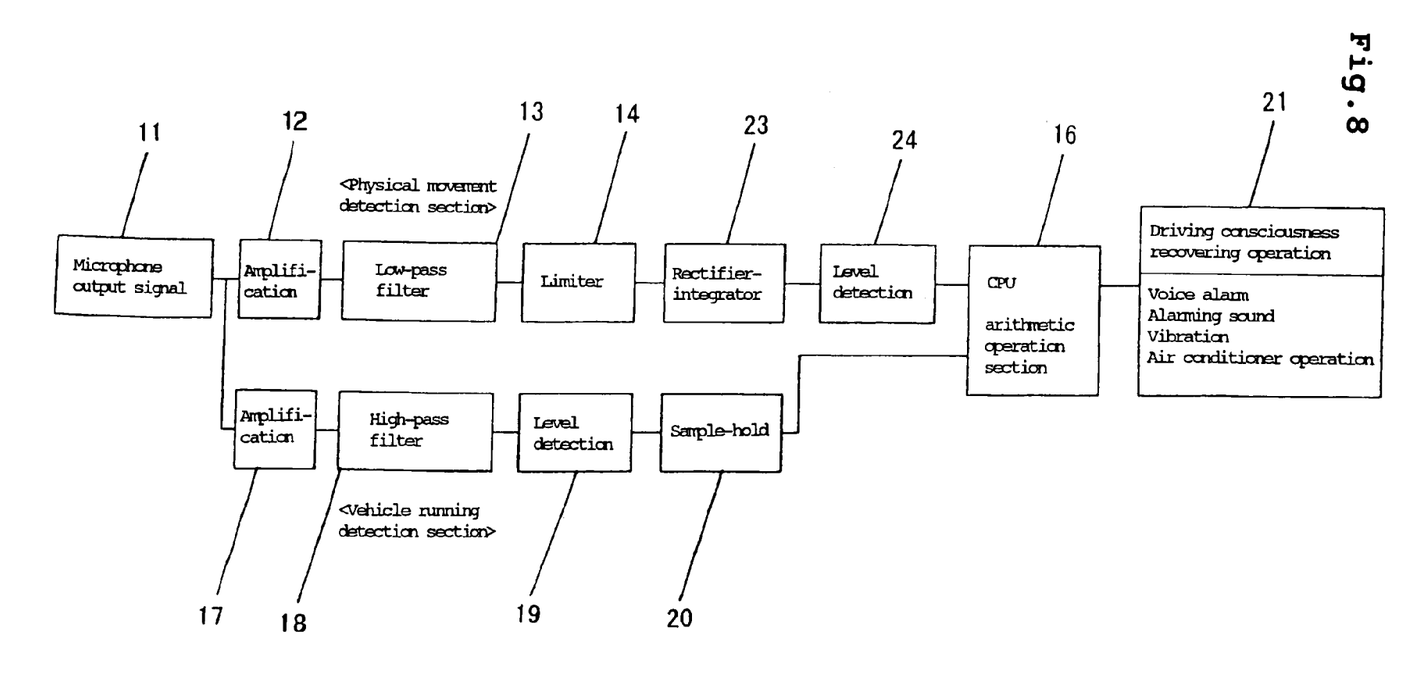
FIG. 8 is a circuit diagram of a further circuit for processing an output of the closed pneumatic sound sensor.
Figure 9:
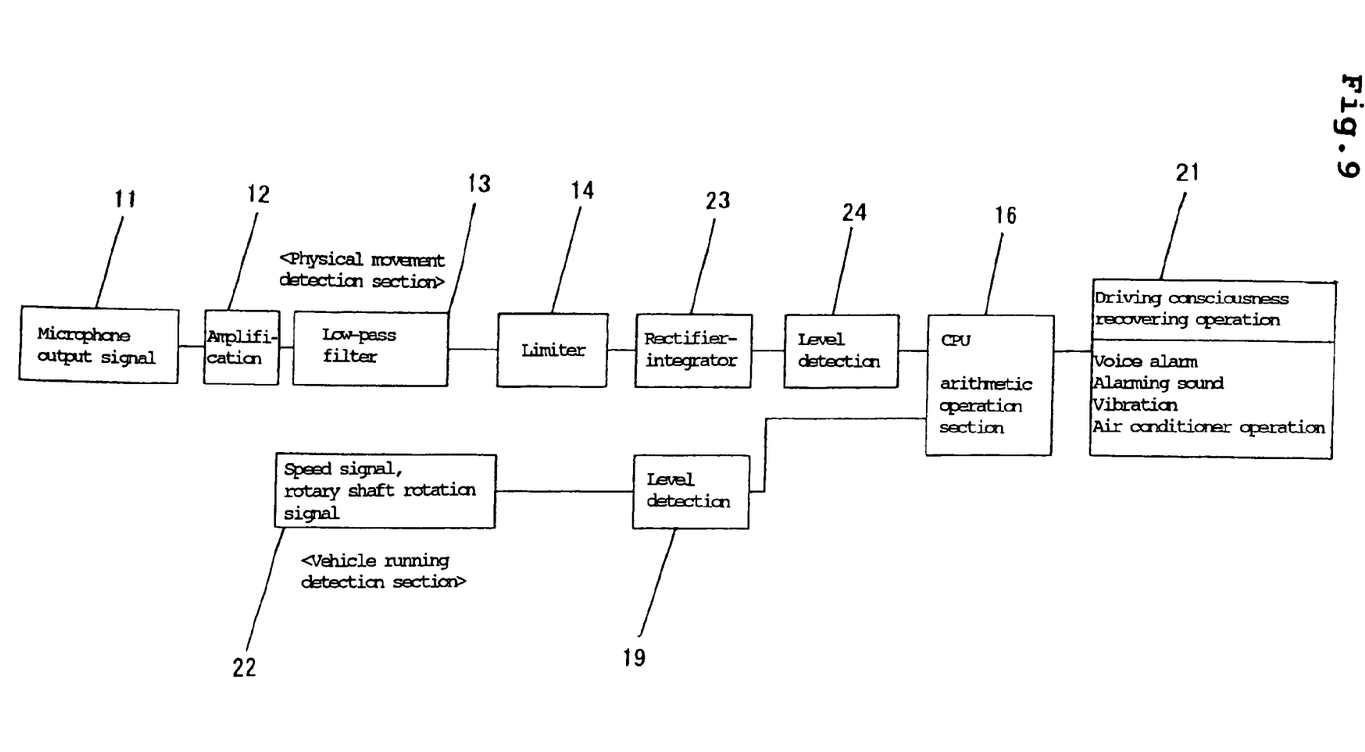
FIG. 9 is a circuit diagram showing a still further circuit for processing an output of the closed pneumatic sound sensor.

FIGS. 8 and 9 are block diagrams showing different examples of the circuit which detects a driving consciousness decline state and generates an alarm signal.

FIG. 8 shows the circuit in a case wherein, similarly to that shown in FIG. 4, a signal representative of a physical movement and a signal representing that the vehicle is operating are separated and extracted from an output of the closed pneumatic sound sensor.

FIG. 9 shows the circuit in another case wherein, similarly as in FIG. 5, a signal representing that the vehicle is operating is extracted from an electric circuit or the like of the vehicle.

In FIGS. 8 and 9, a rectifier-integrator 23 and a level detector 24 are added in place of the counter 15 of FIGS. 4 and 5.

Figure 10:
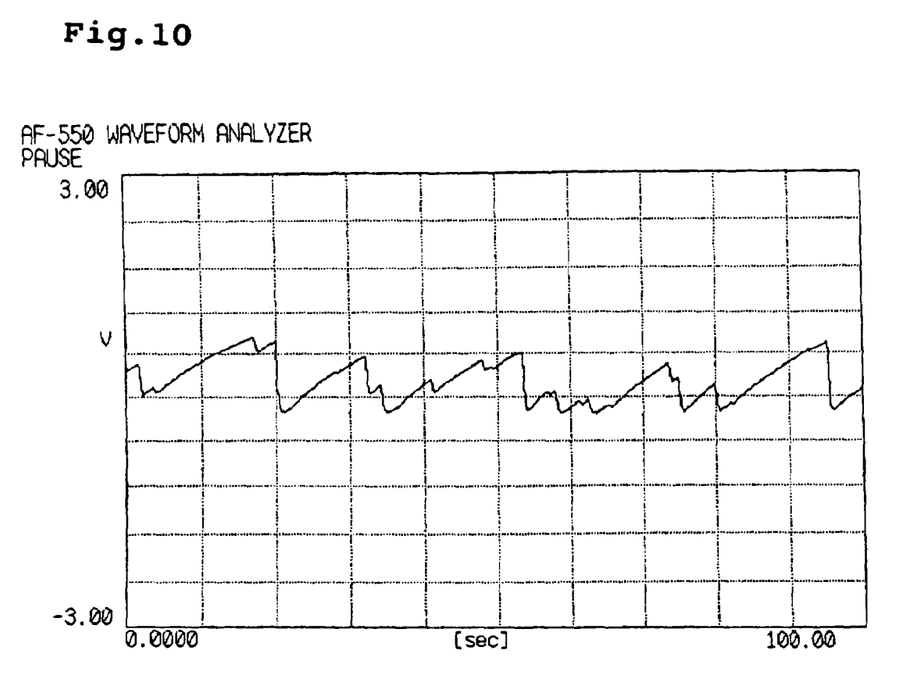
FIG. 10 is a graph illustrating an output of a signal representative of a physical movement in an awakening state.

FIG. 10 is a graph showing a waveform after the signal (FIG. 6) representative of a physical movement in an awakening state further passes the rectifier-integrator 23. When the signal representative of a physical movement exceeds ±200 mV, the integrator formed from a capacitor and a resistor operates, and the signal is formed by subtracting the integrated voltage from a reference voltage. Accordingly, if a signal of ±200 mV or more is inputted frequently, then the signal varies with a low potential level.

Figure 11:
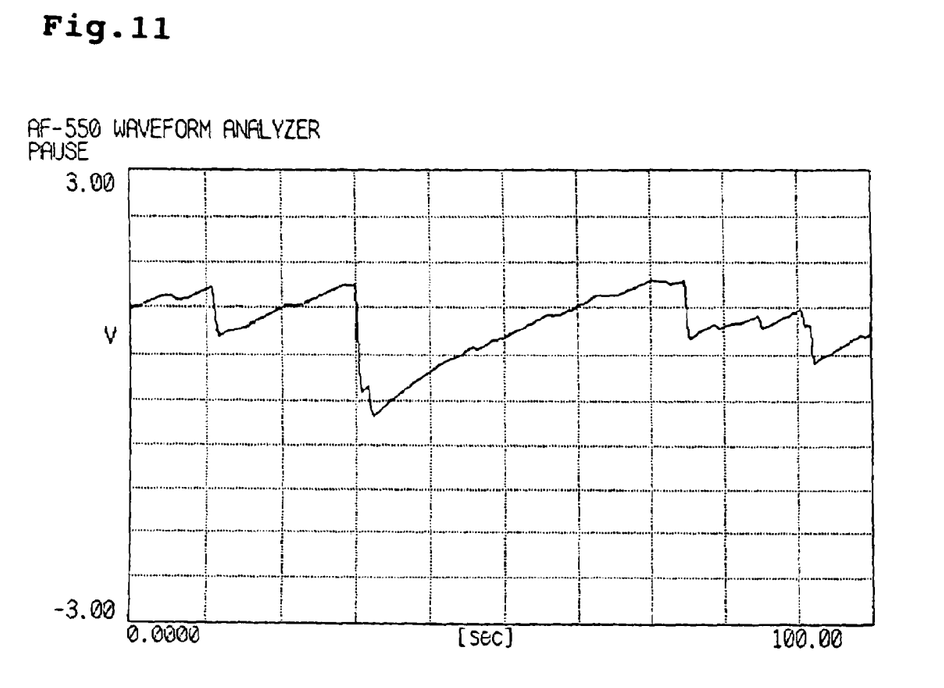
FIG. 11 is a graph illustrating an output of a signal representative of a physical movement in a driving consciousness decline state.

FIG. 11 shows a waveform after the signal (FIG. 7) representative of a driving consciousness decline state passes the rectifier-integrator 23. If the signal representative of the physical movement continues with less than ±200 mV, then the integrated voltage decreases, and the signal changes to a higher voltage level signal with respect to the continuity time.

In the examples of FIGS. 8 and 9, an output signal of the low-pass filter 13 is applied to the limiter 14, and only a limiter passing signal after an influence by a slow driving operation or eupnea is removed is applied to the rectifier-integrator 23.

In a driving consciousness decline state, a slow driving operation or eupnea continues, and it is a characteristic that a signal drop continuation time of lower than 200 mV for more than 15 seconds appears repetitively by two or three times for every minute.

In order to detect this state, by first detecting the signal level in an awakening state by means of the rectifier-integrator and then subtracting the signal in an awakening state from the reference signal, a signal in a driving consciousness decline state can be obtained.

Figure 12:
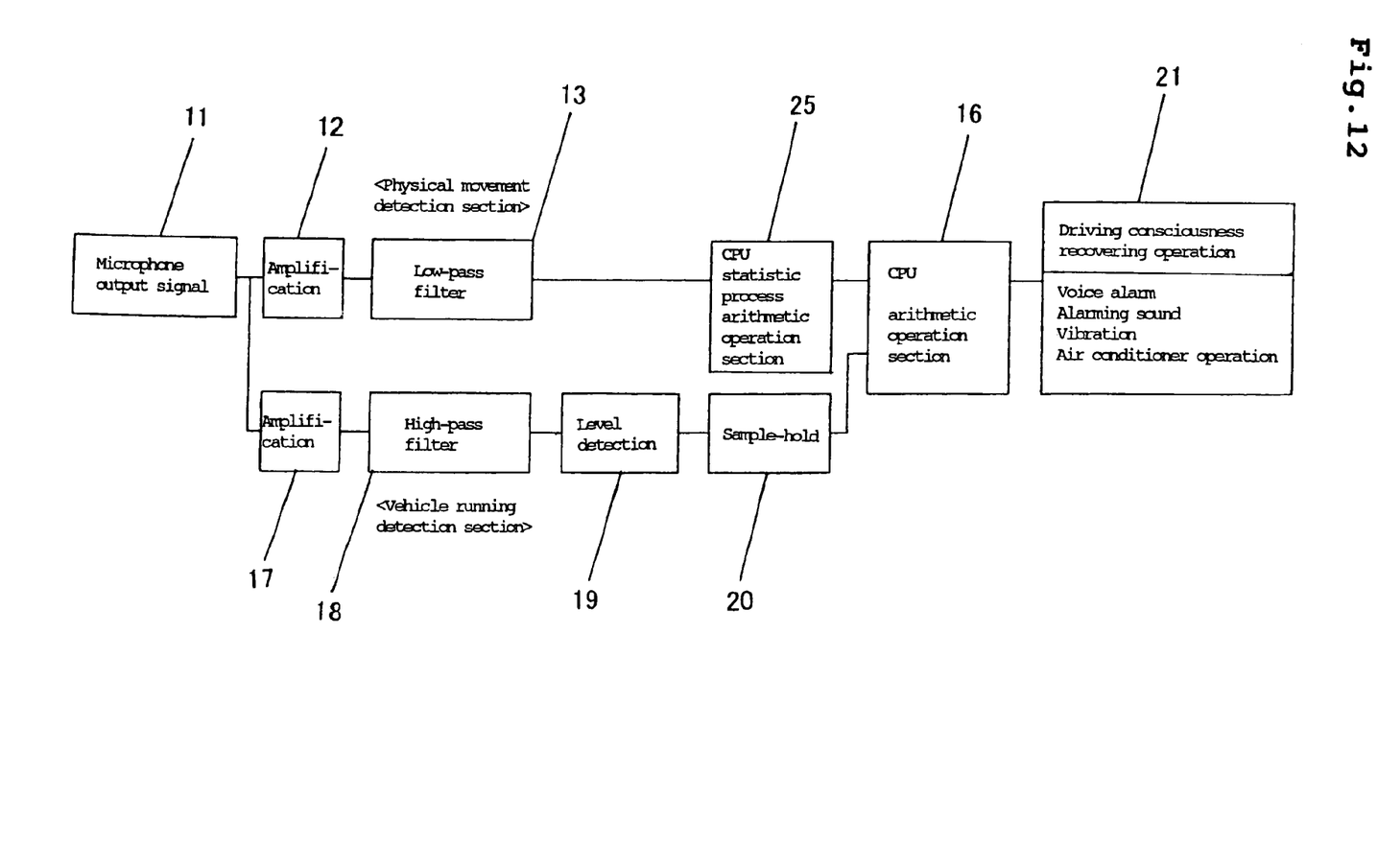
FIG. 12 is a circuit diagram of a yet further circuit for processing an output of the closed pneumatic sound sensor.

FIG. 12 is a block diagram showing a different circuit example which achieves a similar object.

In FIG. 12, a statistic process arithmetic operation section 25 is added in place of the limiter 14, rectifier-integrator 23 and level detector 24 of FIG. 8.

In the embodiment of FIG. 12, the output distribution of a signal at a stage after it passes through the low-pass filter 13 shown in FIGS. 6 and 7 is processed by the statistic process arithmetic operation section 25 to obtain a standard deviation.

Figure 13:
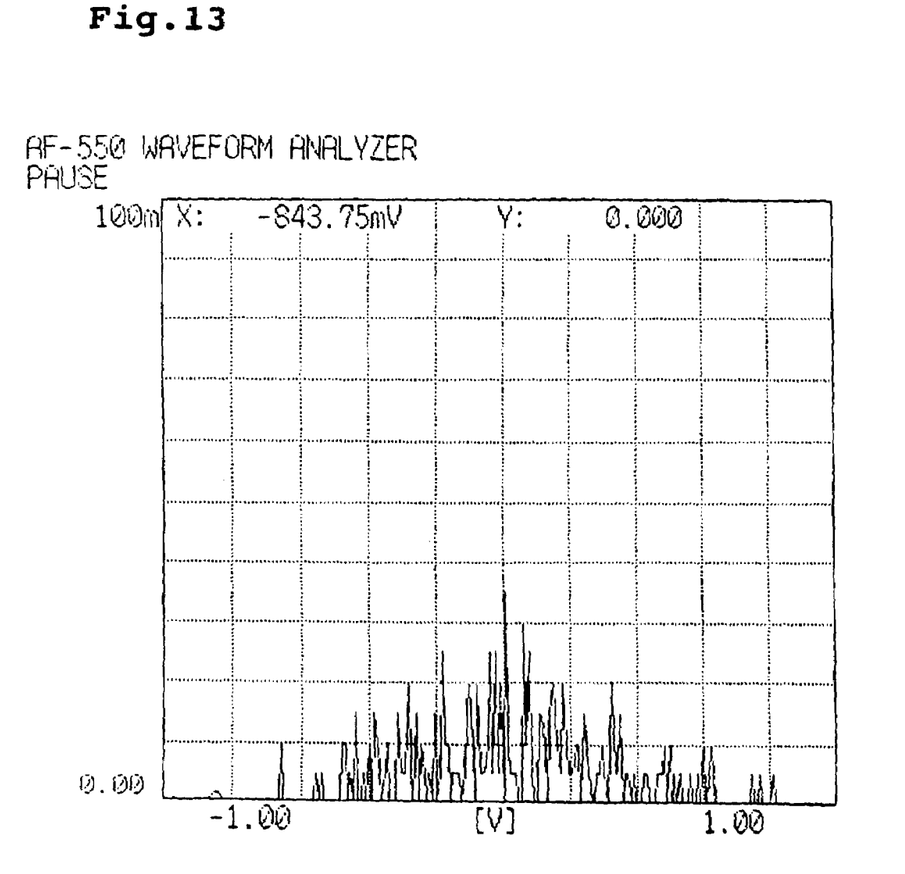
FIG. 13 is a graph illustrating an output of a signal representative of a physical movement in an awakening state.

FIG. 13 illustrates a standard deviation determined with regard to the waveform of FIG. 6, and the standard deviation of the output signal in an awakening state is 0.29.

Figure 14:
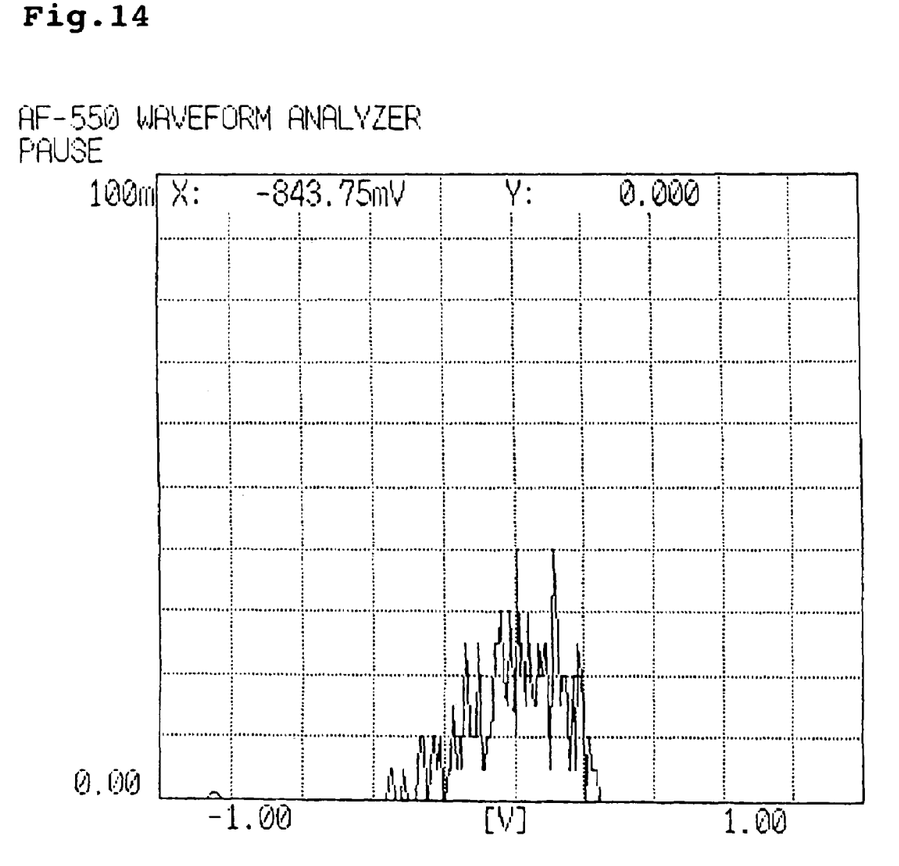
FIG. 14 is a graph illustrating an output of a signal representative of a physical movement in a driving consciousness decline state.

FIG. 14 illustrates a standard deviation determined with regard to the waveform of FIG. 7, and the standard deviation in a driving consciousness decline state is 0.13.

Accordingly, a driving consciousness decline state can be detected also from a drop of the standard deviation value within a fixed period of time which signifies a drop of the signal level.

It can be recognized that, in the present example, the standard deviation value for 40 seconds drops down to less than 50%.

Where the apparatus of the present invention is attached to a driver's seat, the driver is immediately placed into a supervised state without performing a special mounting or dismounting operation when the driver is seated on the driver's seat and an alarming unit does not operate except when the vehicle is.

The invention claimed is:

1. A driver's doze alarm apparatus, wherein
   a closed pneumatic sound sensor wherein one or more non-directional microphones or pressure sensors are enclosed in the inside of a closed airbag or enclosure made of an airtight flexible material and output signals of said non-directional microphones or pressure sensors are extracted to the outside through leads, is attached to a portion of a driver's seat of a vehicle to which a physical pressure of a driver is applied, and
   a signal representative of a physical movement involved in a driving operation of the driver and a signal generated upon running of the vehicle are separated and extracted from an output signal or signals of said closed pneumatic sound sensor, whereafter
   a driving consciousness decline state wherein the signal generated upon running of the vehicle is present and a variation of the signal representative of the physical movement almost disappears is detected and
   an alarm unit is rendered operating.

2. A driver's doze alarm according to claim 1, wherein a reinforcing material of an elastic body is provided in the inside of the closed airbag or enclosure made of the airtight flexible material.

3. A driver's doze alarm apparatus according to claim 1, wherein the plurality of closed pneumatic sound sensors are used.

4. A driver's doze alarm apparatus, wherein
   a closed pneumatic sound sensor wherein internal air pressure of a closed airbag or enclosure made of an airtight flexible material is introduced to an external non-directional microphone or pressure sensor and an output signal of said non-directional microphone or pressure sensor is extracted, is attached to a portion of a driver's seat of a vehicle to which a physical pressure of a driver is applied, and
   a signal representative of a physical movement involved in a driving operation of the driver and a signal generated upon running of the vehicle are separated and extracted from an output signal or signals of said closed pneumatic sound sensor, whereafter
   a driving consciousness decline state wherein the signal generated upon running of the vehicle is present and a variation of the signal representative of the physical movement almost disappears is detected and
   an alarm unit is rendered operating.

5. A driver's doze alarming apparatus according to claim 4, wherein a reinforcing material of an elastic body is provided in the inside of the closed airbag or enclosure made of the airtight flexible material.

6. A driver's doze alarm apparatus according to claim 4, wherein a plurality of closed pneumatic sound sensors are used.

7. A driver's doze alarm apparatus, wherein
   a closed pneumatic sound sensor wherein one or more non-directional microphones or pressure sensors are enclosed in the inside of a closed airbag or enclosure made of an airtight flexible material and output signals of said non-directional microphones or pressure sensors are extracted to the outside through leads, is attached to a portion of a driver's seat of a vehicle to which a physical pressure of a driver is applied, and
   a signal representative of a physical movement of a driver involved in a driving operation of the driver is extracted from said closed pneumatic sound sensor and simultaneously a signal generated upon running of a vehicle is extracted from a body of the vehicle, whereafter
   a driving consciousness decline state wherein the signal generated upon running of the vehicle is present and a variation of the signal representative of the physical movement almost disappears is detected and
   an alarm unit is rendered operating.

8. A driver's doze alarm apparatus according to claim 7, wherein a reinforcing material of an elastic body is provided in the inside of the closed airbag or enclosure made of the airtight flexible material.

9. A driver's doze alarm apparatus according to claim 7, wherein a plurality of closed pneumatic sound sensors are used.

10. A driver's doze alarm apparatus, wherein
    a closed pneumatic sound sensor wherein an internal air pressure of a closed airbag or enclosure made of an airtight flexible material is introduced to an external non-directional microphone or pressure sensor and an output signal of said non-directional microphone or pressure sensor is extracted, is attached to a portion of a driver's seat of a vehicle to which a physical pressure of a driver is applied, and a signal representative of a physical movement of a driver involved in a driving operation of the driver is extracted from said closed pneumatic sound sensor and simultaneously a signal generated upon running of a vehicle is extracted from a body of the vehicle, whereafter a driving consciousness decline state wherein the signal generated upon running of the vehicle is present and a variation of the signal representative of the physical movement almost disappears is detected and an alarm unit is rendered operating.

11. A driver's doze alarm apparatus according to claim 10, wherein a reinforcing material of an elastic body is provided in the inside of the closed airbag or enclosure made of the airtight flexible material.

12. A driver's doze alarm apparatus according to claim 10, wherein a plurality of closed pneumatic sound sensors are used.

13. An alarm for a driver's seat in a vehicle to alert a dozing driver, comprising:

an airtight flexible airbag or enclosure including at least one sensor which senses pressure exerted by a driver sifting in the driver's seat, the at least one sensor generating an output signal representing physical movement of the driver while driving the vehicle, and a motion signal corresponding to motion of the vehicle; the sensor having at least one lead for extracting the signals to the outside of the airbag or enclosure;

means for separating the motion signal from the output signal;

a circuit for detecting a decline in the output signal while the vehicle is in motion corresponding to a loss of consciousness of the driver to sound an alarm.

14. A dozing driver alarm as set forth in claim 13, wherein the sensor is a closed pneumatic sound sensor.

15. A dozing driver alarm as set forth in claim 13, wherein the decline corresponds to a decrease of a standard deviation in a wave form representing the output signal when a driver is awake and the output signal when the driver is asleep.

* * * * *